United States Patent
Vasquez et al.

(10) Patent No.: US 12,070,515 B2
(45) Date of Patent: Aug. 27, 2024

(54) SILICONE FREE EMULSION-BASED PERSONAL CARE COMPOSITIONS AND METHODS FOR THE SAME

(71) Applicant: Colgate-Palmolive Company, New York, NY (US)

(72) Inventors: Elizabeth Vasquez, South Bound Brook, NJ (US); Christine Boyke, Somerset, NJ (US); Nadia Soliman, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 244 days.

(21) Appl. No.: 17/413,595

(22) PCT Filed: Dec. 14, 2018

(86) PCT No.: PCT/US2018/065733
§ 371 (c)(1),
(2) Date: Jun. 14, 2021

(87) PCT Pub. No.: WO2020/122941
PCT Pub. Date: Jun. 18, 2020

(65) Prior Publication Data
US 2022/0040057 A1 Feb. 10, 2022

(51) Int. Cl.
*A61K 8/44* (2006.01)
*A61K 8/06* (2006.01)
*A61K 8/86* (2006.01)
*A61Q 19/00* (2006.01)

(52) U.S. Cl.
CPC .............. *A61K 8/06* (2013.01); *A61K 8/442* (2013.01); *A61K 8/86* (2013.01); *A61Q 19/00* (2013.01); *A61K 2800/34* (2013.01); *A61K 2800/596* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 4,316,902 A | 2/1982 | Yu et al. | |
| 6,193,956 B1 | 2/2001 | Liu et al. | |
| 6,488,916 B1 | 12/2002 | Fowler | |
| 9,750,668 B2 | 9/2017 | Strauss et al. | |
| 2004/0234592 A1* | 11/2004 | Carlsson | A61P 17/00 514/567 |
| 2006/0116489 A1 | 6/2006 | Lennon | |
| 2007/0110791 A1* | 5/2007 | Myhra | A61Q 19/10 424/443 |
| 2010/0189674 A1 | 7/2010 | Morrison et al. | |
| 2012/0259010 A1 | 10/2012 | Misso | |
| 2012/0269867 A1 | 10/2012 | Jimenez et al. | |
| 2013/0276810 A1* | 10/2013 | Hoffmann | A61K 8/39 8/405 |
| 2017/0290748 A1* | 10/2017 | Skubsch | A61K 8/062 |

FOREIGN PATENT DOCUMENTS

| | | |
|---|---|---|
| CA | 2701378 | 10/2011 |
| EP | 1800715 | 6/2007 |
| EP | 2471505 | 7/2012 |
| EP | 3295931 | 3/2018 |
| KR | 20120058846 | 6/2012 |
| WO | 2005/016307 | 2/2005 |
| WO | 2014/163896 | 10/2014 |
| WO | 2019/048193 | 9/2017 |

OTHER PUBLICATIONS

Carrefour—CMI, 2018, "Non Rinsing Nourishing Care", Mintel Database GNPD AN: 5397515.
Coner, 2017, "Firming Buttocks Cream", Mintel Database GNPD AN: 4817371.
Copomon Enterprises, 2017, "PicturePerfect Hair Bond Sealing Masque", Mintel Database GNPD AN: 5157481.
International Search Report and the Written Opinion of the International Searching Authority issued in International Application PCT/US2019/059439 dated Jul. 23, 2020.
Mohiuddin, 2019, "Skin Care Creams: Formulation and Use", Dermatology Clinics & Research, pp. 238-271.
Oriental Aroma, 2014, "Hair Conditioner", Mintel Database GNPD AN: 2388921.
Delarom, 2014, "Moisturising Body Lotion with Passiflora," Mintel GNPD AN: 2748729.
International Search Report and Written Opinion of the International Searching Authority in International Application No. PCT/US2018/065733, dated Aug. 28, 2019.
Simon et al., 2013, "Interpreting DSC Curves Part I: Dynamic Measurements," Usercom website http://.masontechnology.ie/x/Usercom_11.pdf.

\* cited by examiner

*Primary Examiner* — Brian Gulledge (57) ABSTRACT

A personal care composition and methods for determining a stability of the personal care composition are disclosed. The personal care composition may include an emulsion of a hydrophobic phase and a hydrophilic phase. The hydrophobic phase may include an emulsifying system including one or more amino acid surfactants, such as a glutamate surfactant.

14 Claims, 2 Drawing Sheets

SILICONE FREE EMULSION-BASED PERSONAL CARE COMPOSITIONS AND METHODS FOR THE SAME

BACKGROUND

Conventional personal care compositions may often include silicon-based polymers, such as polymethylsiloxane or dimethicone, to provide skin conditioning, anti-foaming, and skin protection. Recent shortages in silicone, however, have resulted in a corresponding increase in the price of silicone. As such, efforts have been directed to reducing or eliminating silicon-based polymers and silicone-based compounds from personal care compositions to provide cost effect products. The removal or replacement of silicon-based polymers, however, has proven to be difficult especially in high viscosity petrolatum based formulations. For example, the removal or replacement of silicon-based polymers in high viscosity petrolatum based formulations often result in products that exhibit instability or phase separation during aging studies. Further, the removal or replacement of silicon-based polymers in the high viscosity petrolatum based formulations also results in a white foaming effect during application.

What is needed, then, are improved silicon-free personal care compositions, and methods for preparing, maintaining, and predicting the stability of the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a personal care composition including an emulsion of a hydrophobic phase and a hydrophilic phase. The hydrophobic phase may include an emulsifying system including one or more amino acid surfactants.

In at least one implementation, the one or more amino acid surfactants may include a glutamate surfactant. The glutamate surfactant may be represented by formula (1), disclosed herein, where $R_1$ is a saturated or unsaturated, straight, or branched alkyl chain comprising 7 to 17 carbon atoms, more preferably, 9 to 13 carbon atoms, and where $M^+$ is each, independently, hydrogen, sodium, or potassium.

In at least one implementation, the emulsifying system may further include glyceryl monostearate and PEG-100 stearate. Each of glyceryl monostearate and PEG-100 stearate may, independently and separately, be present in an amount of at least 1.5 weight %, optionally, at least 1.75 weight %, based on a total weight of the personal care composition.

In at least one implementation, the emulsifying system may further include one or more fatty alcohols. The fatty alcohols may include cetyl alcohol. The cetyl alcohol may be present in an amount of from about 3 weight % to about 4 weight %, based on a total weight of the personal care composition.

In at least one implementation, the hydrophobic phase may further include a hydrophobic carrier. The hydrophobic carrier may include petrolatum.

In at least one implementation, the personal care composition may be substantially free of dimethicone. In another implementation, the personal care composition is substantially free of silicone and silicone compounds.

In at least one implementation, the hydrophilic phase may include water.

In at least one implementation, the hydrophilic phase includes one or more acids. The one or more acids may include lactic acid.

In at least one implementation, the personal care composition may have an acidic pH. The pH may be from about 4 to about 6 or from about 4 to about 5.

In at least one implementation, the personal care composition may have a viscosity of greater than or equal to 50,000 centipoise (cP) at 25° C.

In at least one implementation, the personal care composition may not exhibit phase separation after exposure to accelerated aging conditions.

In at least one implementation, the personal care composition has any one or more of the following properties, as determined by an Small Sensory Panel using a standardized methodology and on a 0 to 5 point assessment scale: a whiteness of less than or equal to 2.7; an absorbability of greater than or equal to 2.7; a spreadability of greater than or equal to 3.0; a tackiness of less than or equal to 2.0; a greasiness of less than or equal to 2.5; or combinations thereof.

The foregoing and/or other aspects and utilities embodied in the present disclosure may be achieved by providing a method for preparing any one of the personal care composition disclosed herein. The method may include emulsifying the hydrophobic phase and the hydrophilic phase with one another. The method may also include heating the hydrophobic phase and the hydrophilic with one another at a temperature of from about 60° C. to about 90° C., about 65° C. to about 85° C., about 70° C. to about 80° C., or about 75° C. to about 80° C.

The foregoing and/or other aspects and utilities embodied in the present disclosure may be achieved by providing a method for determining a stability of a personal care composition. The method may include exposing the personal care composition to at least two heating and cooling cycles in a differential scanning calorimeter. The method may also include generating a first differential scanning calorimetry curve from a first heating and cooling cycle. The method may further include generating a second differential scanning calorimetry curve from a second heating and cooling cycle. The method may also include comparing the first differential scanning calorimetry curve with the second differential scanning calorimetry curve. Comparing the first differential scanning calorimetry curve with the second differential scanning calorimetry curve may include comparing a slope and/or a peak intensity of the first differential scanning calorimetry curve and the second differential scanning calorimetry curve with one another. The method may also include outputting the stability of the personal care composition. Any one or more of the steps described above may be performed by an electronic processor.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF THE DRAWINGS

The present disclosure is best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any implementations or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that stable silicone free personal care compositions may be prepared by including glyceryl monostearate in amounts relatively greater than PEG-100 stearate. The present inventors have also surprisingly and unexpectedly discovered a method for predicting the stability of personal care compositions that is reliable and relatively faster than testing under accelerated aging conditions.

Compositions

Compositions disclosed herein may be or include stable, emulsion-based personal care composition including a glutamate surfactant. The compositions disclosed herein may be free or substantially free of silicone and compounds thereof. For example, the compositions disclosed herein may be or include a skin moisturizing composition, such as an emulsion-based skin moisturizing composition or emulsion-based lotion or cream, that is free or substantially free of silicone and silicone compounds, and includes a glutamate surfactant. The personal care compositions disclosed herein may exhibit comparable, enhanced, or relatively greater stability as compared to conventional personal care compositions including silicone and/or silicone compounds. For example, the personal care compositions disclosed herein may exhibit no phase separation, relatively stable pH, and/or relatively stable viscosity when exposed to various aging conditions. As used herein, the term or expression "relatively stable" may refer to a property or value that does not change (e.g., increase or decrease) from an original property or value by an amount greater than 1%, greater than 2%, greater than 3%, greater than 4%, greater than 5%, or greater than 10%. The personal care compositions disclosed herein may also exhibit acceptable and/or sufficient whiteness, absorbability, spreadability, tackiness, and/or greasiness, as determined by a Small Sensory Panel. As further described herein, the personal care composition may include an emulsifying system including one or more surfactants and/or emulsifiers capable of or configured to provide comparable or enhanced stability to the personal care composition as compared to conventional personal care compositions including silicone or silicone compounds.

The personal care composition may include a hydrophobic phase and a hydrophilic phase combined, mixed, contacted, or otherwise emulsified with one another. For example, the personal care composition may be a water-in-oil emulsion including a hydrophilic phase dispersed or suspended in a continuous hydrophobic phase. In another example, the personal care composition may be an oil-in-water emulsion including a hydrophobic phase dispersed or suspended in a continuous hydrophilic phase. In a preferred implementation, the personal care composition is an oil-in-water emulsion including a hydrophobic phase suspended in a continuous hydrophilic phase.

The personal care composition may have an acidic pH. For example, the personal care composition may have a pH of from about 3, about 3.5, about 4, or about 4.5 to about 5, about 5.5, about 6, or about 6.5. In another example, the personal care composition may have a pH of less than 7, less than 6.5, less than 6, less than 5.5, less than 5, or less than 4.5. In a preferred implementation, the personal care composition may have a pH of from about 4.0 to about 5.0, or about 4.2 to about 4.8, more preferably about 4.2 to about 4.6.

As used herein, the term or expression "absorbability" may refer to the speed or how quick the personal care composition is absorbed into the skin. The personal care composition may have an absorbability score or value of greater than or equal to about 2.0, as determined by an Small Sensory panel using a standardized methodology and a 0 to 5 point assessment scale, where '0' represented the lowest level (i.e., none or low) and '5' represented the highest value. For example, the personal care composition may have an absorbability score of greater than or equal to about 2.0, greater than or equal to about 2.2, greater than or equal to about 2.4, greater than or equal to about 2.6, greater than or equal to about 2.8, greater than or equal to about 3.0, greater than or equal to about 3.2, greater than or equal to about 3.4, greater than or equal to about 3.6, greater than or equal to about 3.8, greater than or equal to about 4.0, as determined by the Small Sensory panel. In a preferred implementation, the personal care composition has an absorbability score of greater than or equal to about 2.7.

As used herein, the term or expression "whiteness" or "whiteness score" may refer to the amount of white perceived to be visible on skin during application or rubbing. The personal care composition may have a whiteness score or value of less than or equal to about 3.6, as determined by an Small Sensory panel using a standardized methodology and a 0 to 5 point assessment scale, where '0' represented the lowest level (i.e., none or low) and '5' represented the highest value. For example, the personal care composition may have a whiteness score of less than or equal to about 3.6, less than or equal to about 3.4, less than or equal to about 3.2, less than or equal to about 3.0, less than or equal to about 2.8, less than or equal to about 2.6, less than or equal to about 2.4, less than or equal to about 2.2, less than or equal to about 2.0, or less than or equal to about 1.8, as determined by the Small Sensory panel. In a preferred implementation, the personal care composition has a whiteness score of less than or equal to about 2.7.

As used herein, the term or expression "tackiness" or "tackiness score" may refer to the sticky feeling left after application of the personal care composition on surfaces of the skin. The personal care composition may have a tackiness score or value of less than or equal to about 3.0, as determined by an Small Sensory panel using a standardized methodology and a 0 to 5 point assessment scale, where '0' represented the lowest level (i.e., none or low) and '5' represented the highest value. For example, the personal care composition may have a tackiness score of less than or equal to about 3.0, less than or equal to about 2.8, less than or equal to about 2.6, less than or equal to about 2.4, less than or equal to about 2.2, less than or equal to about 2.0, less than or equal to about 1.8, less than or equal to about 1.6, less than or equal to about 1.4, as determined by the Small Sensory panel. In a preferred implementation, the personal care composition has a tackiness score of less than or equal to about 2.0.

As used herein, the term or expression "spreadability" or "spreadability score" may refer to how easily or the ease at which the personal care composition is distributed on surfaces of the skin. The personal care composition may have a spreadability score or value of greater than or equal to about 2.0, as determined by an Small Sensory panel using a standardized methodology and a 0 to 5 point assessment scale, where '0' represented the lowest level (i.e., none or low) and '5' represented the highest value. For example, the personal care composition may have a spreadability score of greater than or equal to about 2.0, greater than or equal to about 2.2, greater than or equal to about 2.4, greater than or equal to about 2.6, greater than or equal to about 2.8, greater than or equal to about 3.0, greater than or equal to about 3.2, greater than or equal to about 3.4, greater than or equal to about 3.6, greater than or equal to about 3.8, greater than or equal to about 4.0, as determined by the Small Sensory panel. In a preferred implementation, the personal care composition has a spreadability score of greater than or equal to about 3.0.

As used herein, the term or expression "greasiness" or "greasiness score" may refer to the amount of greasiness felt on surfaces of the skin during and/or after application. The personal care composition may have a greasiness score or value of less than or equal to about 3.6, as determined by an Small Sensory panel using a standardized methodology and a 0 to 5 point assessment scale, where '0' represented the lowest level (i.e., none or low) and '5' represented the highest value. For example, the personal care composition may have a greasiness score of less than or equal to about 3.6, less than or equal to about 3.4, less than or equal to about 3.2, less than or equal to about 3.0, less than or equal to about 2.8, less than or equal to about 2.6, less than or equal to about 2.4, less than or equal to about 2.2, less than or equal to about 2.0, or less than or equal to about 1.8, as determined by the Small Sensory panel. In a preferred implementation, the personal care composition has a greasiness score of less than or equal to about 2.5.

The personal care composition may have a viscosity, as determined using a viscometer at a temperature of about 25° C., of greater than or equal to about 100,000 centipoise (cP). As used herein, the term "viscosity" may refer to the internal resistance to flow exhibited by a fluid or the ratio of shearing stress to rate of shear, and may be measured in poise or centipoises (cP). For example, the personal care composition may have a viscosity of greater than or equal to about 105,000 cP, greater than or equal to about 110,000 cP, greater than or equal to about 115,000 cP, greater than or equal to about 120,000 cP, greater than or equal to about 125,000 cP, greater than or equal to about 130,000 cP, greater than or equal to about 135,000 cP, greater than or equal to about 140,000 cP, greater than or equal to about 145,000 cP, greater than or equal to about 150,000 cP, greater than or equal to about 155,000 cP, or greater, at about 25° C. In a preferred implementation, the personal care composition has a viscosity of greater than or equal to about 120,000 cP.

The personal care composition may not exhibit any phase separation, as determined visually, after aging for 5 days at about 10° C., after aging for 5 days at about 30° C., and/or after exposure to accelerated aging conditions.

In an exemplary implementation, the personal care composition may include any one or more of the following properties: a pH of about 4.2 to about 4.6, an absorbability score of greater than or equal to about 2.7, a whiteness score of less than or equal to about 2.7, a tackiness score of less than or equal to about 2.0, a spreadability score of greater than or equal to about 3.0, a greasiness score of less than or equal to about 2.5, a viscosity of greater than or equal to about 120,000 cP, no phase separation after aging for 5 days at about 10° C., after aging for 5 days at about 30° C., and/or after exposure to accelerated aging conditions, or any combination thereof.

In an exemplary implementation, the personal care composition may be free or substantially free of silicone or silicone compounds. Illustrative silicone or silicone compounds may be or include, but are not limited to, polysiloxane polymers, such as dimethicone, dimethiconol, cyclopentasiloxane, or any combination thereof.

Hydrophilic Phase

The hydrophilic phase of the personal care composition may include water. Water of the hydrophilic phase may be deionized water, demineralized water, and/or softened water. In an exemplary implementation, the hydrophilic phase includes demineralized water and softened water. Water may make up the balance of the personal care composition. For example, the amount of water present in the personal care composition may be greater than 60 weight %, greater than 65 weight %, greater than 70 weight %, greater than 75 weight %, greater than 80 weight %, greater than 85 weight %, greater than 90 weight %, greater than 92 weight %, greater than 94 weight %, or greater than 96 weight %, based on a total weight of the personal care composition or the hydrophilic phase thereof. The amount of water in the personal care composition may include free water added and water introduced with other components or materials of the personal care composition. For example, the amount of the water in the personal care composition may include free water and water associated with one or more surfactants and/or any other components of the personal care composition.

In at least one implementation, hydrophilic phase may include one or more humectants. Illustrative humectants may be or include, but are not limited to, glycerin, propylene glycol, polyethylene glycol, ascorbic acid, ascorbyl dipalmitate, acetamide MEA, caprylyl glycol, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, or the like, or combinations thereof. In a preferred implementation, the humectants may be or include, but is not limited to, glycerin and/or propylene glycol.

The humectant may be present in an amount of from about 0.5 weight % to about 10 weight % or from about 0.5 weight % to about 20 weight %, based on a total weight of the personal care composition or the hydrophilic phase thereof. For example, the humectant (e.g., glycerin and/or propylene glycol) may be present in an amount of from about 0.5 weight %, about 1 weight %, about 1.5 weight %, about 2 weight %, about 2.5 weight %, about 3 weight %, about 3.5 weight %, about 4 weight %, about 4.5 weight %, or about 5 weight % to about 5.5 weight %, about 6 weight %, about 6.5 weight %, about 7 weight %, about 7.5 weight %, about 8 weight %, about 8.5 weight %, about 9 weight %, about 9.5 weight %, about 10 weight %, or about 20 weight %, based on a total weight of the personal care composition or the hydrophilic phase thereof. In a preferred implementation, the humectant includes glycerin and/or propylene glycol in an amount of from about 1.5 to about 10 weight %, about 3 weight % to about 8 weight %, about 5 weight % to about 7 weight %, or about 6 weight %, based on a total weight of the personal care composition or the hydrophilic phase thereof.

The hydrophilic phase may include one or more preservatives in an amount greater than 0 weight % and less than or equal to about 3 weight %, less than or equal to about 2.5 weight %, less than or equal to about 2 weight %, less than or equal to about 1.5 weight %, less than or equal to about 1 weight %, less than or equal to about 0.75 weight %, less than or equal to about 0.5 weight %, or less than or equal to about 0.25 weight %, based on a total weight of the personal care composition or the hydrophilic phase thereof. Illustrative preservatives may include, but are not limited to, benzalkonium chloride; benzethonium chloride, 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5,5-dimethyl hydantoin; formaldehyde; iodopropynl butyl carbamate, butyl paraben; ethyl paraben; methyl paraben; propyl paraben, mixture of methyl isothiazolinone/methyl-chloroisothiazoline in a 1:3 wt. ratio; mixture of polyvinylpyrro/butyl paraben/methyl paraben/propylparaben; 2-phenoxyethanol; tris-hydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadam-antane chloride; sodium benzoate; organic acids, sorbic acid, lactic acid, citric acid, or the like, or combinations thereof.

In at least one implementation, the preservative includes sodium benzoate in an amount of from greater than 0 weight % to less than or equal to 2 weight %, greater than 0 weight % to less than or equal to 1 weight %, or about 0.5 weight %, based on a total weight of the personal care composition or the hydrophilic phase thereof. In yet another implementation, the preservative includes sodium benzoate in an amount of from greater than 0 weight % to less than or equal to 2 weight %, greater than 0 weight % to less than or equal to 1 weight %, or greater than 0 weight % to less than or equal to 0.8 weight %, based on a total weight of the personal care composition or the hydrophilic phase thereof. For example, the hydrophilic phase may include sodium benzoate in an amount of about 0.3 weight % and sodium benzoate in an amount of about 0.5 weight %, based on a total weight of the personal care composition or the hydrophilic phase thereof. In at least one implementation, the personal care compositions and/or the preservative system thereof may be free or substantially free of phenoxyethanol.

In at least one implementation, the hydrophilic phase may include one or more acids, one or more bases, and/or one or more buffers configured to adjust or control the pH of the personal care composition or the hydrophilic phase thereof. The one or more acids, one or more bases, and/or one or more buffers may, separately and independently, be present in an amount of from greater than 0 weight % to less than or equal to about 5 weight %, less than or equal to about 4 weight %, less than or equal to about 3 weight %, less than or equal to about 2 weight %, less than or equal to about 1 weight %, less than or equal to about 0.75 weight %, less than or equal to about 0.5 weight %, less than or equal to about 0.4 weight %, or less than or equal to about 0.35 weight %, based on a total weight of the personal care composition or the hydrophilic phase thereof. Illustrative bases may include, but are not limited to, ammonia; mono-, di-, and tri-alkyl amines; mono-, di-, and tri-alkanolamines; alkali metal and alkaline earth metal hydroxides; sodium hydroxide, potassium hydroxide, lithium hydroxide, monoethanolamine, triethylamine, isopropanolamine, diethanolamine, triethanolamine, or the like, or combinations thereof. Illustrative acids may include, but are not limited to, mineral acids, such as hydrochloric acid, nitric acid, phosphoic acid, and sulfuric acid, organic acids, polycarboxylic acids, such as citric acid, glycolic acid, and lactic acid, or the like, or combinations thereof. In a preferred implementation, the hydrophilic phase includes at least one acid, such as lactic acid, and the lactic acid is present in an amount of from greater than 0 weight % to about 0.5 weight %, or about 0.35 weight %, based on a total weight of the personal care composition or the hydrophilic phase thereof.

In at least one implementation, the personal care composition and the emulsifying system thereof may include one or more amino acid surfactants, such as glutamate surfactants (e.g., sodium stearoyl glutamate) and be free or substantially free of other anionic surfactants, such as stearic acid, or the like. It should be appreciated that utilizing the anionic surfactant, stearic acid, as in conventional personal care compositions, may often require the neutralization of the stearic acid with a base, such as triethanolamine. As such, by providing a personal care composition that is free or substantially free of stearic acid, the personal care compositions disclosed herein may also be free or substantially free of triethanolamine. It should further be appreciated that conventional personal care compositions that include stearic acid and/or triethanolamine may not be capable of providing a pH of from about 4 to about 6 or about 4 to about 5, as the subsequent addition of an acid, such as lactic acid, results in precipitation or phase separation of the personal care composition. As such, the homogenous, stable personal care compositions and methods for preparing the personal care compositions disclosed herein, may be free or substantially free of steric acid and/or triethanolamine, and may further maintain a pH of from about 4 to about 6, or about 4 to about 5 (via the addition of one or more acids, such as lactic acid). Further, the stable personal care compositions disclosed herein may not exhibit any phase separation and/or precipitate formation (precipitation) after exposure to aging conditions.

Hydrophobic Phase

The hydrophobic phase of the personal care composition may include one or more acceptable or suitable carriers in an amount of from about greater than 0 weight % to less than or equal to about 5 weight %, about 1 weight % to about 4 weight %, about 2 weight % to about 3 weight %, or about 2.5 weight %, based on a total weight of the personal care composition or the hydrophobic phase thereof. Any suitable carriers or hydrophobic materials that do not adversely affect the stability and/or efficacy of the personal care composition may be used. Illustrative carriers or hydrophobic materials may include, but are not limited to, isopropyl myristate, waxes such as bees wax, mineral oil, plastigel, a blend of mineral oil and polyethylene, petrolatum, white petrolatum, soft paraffin/paraffin wax, versagel (blend of liquid paraffin, butene/ethylene/styrene hydrogenated copolymer), acrylate and vinyl acetate polymers and copolymers, polyethylene waxes, and polyvinyl pyrrolidone/vinyl acetate copolymers, or the like, or any combination thereof.

The hydrophobic phase may include an emulsifying system including one or more surfactants and/or one or more emulsifiers configured to provide enhanced or relatively greater stability to the personal care composition, as compared to conventional personal care compositions. The one or more surfactants and/or emulsifiers may include one or more amino acid-based surfactants, one or more anionic surfactants, one or more cationic surfactants, one or more zwitterionic surfactants, one or more nonionic surfactants, or mixtures thereof.

Illustrative amino acid surfactants may be or include glutamate surfactants, alanine surfactants, aspartate surfactants, or the like, or any mixture or combination thereof. Illustrative glutamate surfactants may be represented by formula (1):

where $R_1$ may be a saturated or unsaturated, straight or branched alkyl chain with 7 to 17 C atoms, and more preferably 9 to 13 C atoms, and $M^+$ may be independent from each other H, sodium or potassium. Illustrative glutamate surfactants may be or include, but are not limited to, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof. Preferred are disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, and sodium myristoyl glutamate and mixtures thereof. More preferred are disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, sodium lauroyl glutamate, or the like, or combinations or mixtures thereof. In a preferred implementation, the personal care composition includes at least sodium stearoyl glutamate.

Illustrative anionic surfactants may include, but are not limited to, stearic acid, water-soluble salts of higher fatty acid monoglyceride monosulfates, such as a sodium salt of a monosulfated monoglyceride of hydrogenated coconut oil fatty acids, such as sodium N-methyl N-cocoyl 14olyviny, sodium cocomonoglyceride sulfate. Illustrative anionic surfactants may also include higher alkyl sulfates. As used herein, "higher alkyl" refers to $C_{6-30}$ alkyl. For example, the anionic surfactant may be or include sodium lauryl sulfate. The anionic surfactants may also include higher alkyl-ether sulfates. In another implementation, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. In an exemplary implementation, the anionic surfactant may be or include a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, or mixtures thereof.

Illustrative nonionic surfactants may be or include, but are not limited to, higher alcohols or fatty alcohols, including straight chain alcohols or ethoxylates thereof, sorbitan fatty acid esters (e.g., sorbitan mono oleate, sorbitan mono isostearate, sorbitan mono laurate, sorbitan mono palmitate, sorbitan mono stearate, sorbitan sesquioleate, sorbitan trioleate, diglycerol sorbitan penta-2-ethylhexylate, diglycerol sorbitan tetra-2-ethylhexylate, etc.); glycerin polyglycerin aliphatic acids (e.g., mono cottonseed oil fatty acid glycerin, glyceryl monoerucate, glycerin sesquioleate, glyceryl monostearate, glyceryl stearate, α, α'-glycerin oleate pyroglutamate, monostearate glycerin malic acid, etc.); propylene glycol fatty acid esters (e.g., propylene glycol monostearatem, etc.); hydrogenated castor oil derivatives; glycerin alkylethers, or the like, or combinations thereof. Illustrative nonionic surfactants may also be or include, but are not limited to, sorbitan esters and ethoxylated sorbitan esters (e.g., PEG-20 sorbitan isostearate, sorbitan monolaurate, polysorbate-20, polysorbate-40, polysorbate-60, polysorbate-80); ethoxylates (e.g., Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, etc.); ethoxylated adducts (e.g., PEG-25 stearate, glyceryl stearate, PEG-100 stearate, etc.); polyoxyethylene (100) monostearate, a polyethylene glycol ester of stearic acid, PEG esters (e.g., PEG-8 oleate, PEG-8 laurate, PEG-8 dilaurate, PEG-12 dilaurate, PEG-80 diisostearate, PEG-40 stearate, etc.); propoxylates (e.g., PPG-10 butanediol, PPG-50 oleyl ether, PPG-2-ceteareth-9, PPG-3-deceth-3, PPG-5-ceteth-20); ethoxylated modified triglycerides (e.g., PEG-20 corn glycerides, PEG-12 palm kernel glycerides); alkylphenol aromatic ethoxylates (e.g., dinonylphenol ethoxylate with 9 moles of EO octylphenol ethoxylate with 20 moles of EO, octylphenol ethoxylate with 40 moles of EO); block copolymers that are alkoxylated glycols having ethoxylated and propoxylated segments (e.g., POLOXAMER™ 182 and 234, POLOXAMER™ 105 Benzoate, and MEROXAPOL™ 174); or the like, or combinations thereof.

Illustrative fatty alcohols or higher alcohols may be or include, but are not limited to, straight chain alcohols, such as a $C_{12-22}$ fatty alcohol, or preferably a $C_{16-18}$ fatty alcohol, lauryl alcohol, myristyl alcohol, cetyl alcohol, behenyl alcohol, stearyl alcohol, cetyl-stearyl alcohol 50/50, or the like, or combinations thereof. Illustrative fatty alcohols may also include branch chain alcohols, such as monostearyl glycerin ether (batyl alcohol), 2-decyltetradecynol, lanolin alcohol, cholesterol, phytosterol, hexyl dodecanol, isostearyl alcohol, octyl dodecanol), or the like, or combinations thereof.

The amount of each of the one or more surfactants and/or emulsifiers present in the personal care composition or the emulsifying system thereof may vary widely. For example, each of the one or more surfactants and/or emulsifiers may, separately and independently, be present in an amount of from about greater than 0 weight % to less than or equal to about 15 weight %, based on a total weight of the personal care composition or the emulsifying system thereof. For example, each of the one or more surfactants and/or emulsifiers may, separately and independently, be present in an amount of from about greater than 0 weight %, 0.25 weight %, about 0.5 weight %, about 0.75 weight %, about 1 weight %, about 1.25 weight %, about 1.5 weight %, about 1.75 weight %, about 2 weight %, about 2.25 weight %, about 2.5 weight %, or about 3 weight % to about 3.5 weight %, about 4 weight %, about 4.5 weight %, about 5 weight %, about 5.5 weight %, about 6 weight %, or greater, based on a total weight of the personal care composition or the emulsifying system thereof. In another example, each of the one or more surfactants and/or emulsifiers may, separately and independently, be present in an amount of from about greater than 0 weight %, about 1 weight %, about 2 weight %, about 3 weight %, about 4 weight %, about 5 weight %, about 6 weight %, or about 7 weight % to about 8 weight %, about 9 weight %, about 10 weight %, about 11 weight %, about 12 weight %, about 13 weight %, about 14 weight %, or about 15 weight %, based on a total weight of the personal care composition or the emulsifying system thereof. In an exemplary implementation, the one or more surfactants and/or emulsifiers present in the personal care composition includes sodium stearoyl glutamate, glyveryl monostearate, cetyl alcohol, PEG-100 stearate, or any combination thereof, in an amount of greater than 0.0 weight % and less than or equal to 15 weight %.

In at least one implementation, each of the one or more surfactants and/or emulsifiers may, separately and independently, be present in an amount of less than or equal to 5 weight %, and greater than 0 weight %, greater than or equal to 1.5 weight %, greater than or equal to 1.75 weight %, greater than or equal to 2 weight %, greater than or equal to 2.25 weight %, greater than or equal to 2.5 weight %, greater than or equal to 2.75 weight %, greater than or equal to 3 weight %, greater than or equal to 3.5 weight %, or greater than or equal to 4 weight %, based on a total weight of the personal care composition or the emulsifying system thereof.

In another implementation, at least two of the one or more surfactants and/or emulsifiers may be present in an amount of greater than or equal to 0.01 weight %, greater than or equal to 1.5 weight %, greater than or equal to 1.75 weight %, greater than or equal to 2 weight %, greater than or equal to 2.25 weight %, greater than or equal to 2.5 weight %, greater than or equal to 2.75 weight %, greater than or equal to 3 weight %, greater than or equal to 3.5 weight %, greater than or equal to 4 weight %, greater than or equal to 4.25 weight %, greater than or equal to 4.5 weight %, greater than or equal to 5 weight %, greater than or equal to 5.5 weight %, greater than or equal to 6 weight %, greater than or equal to 6.5 weight %, greater than or equal to 7 weight %, greater than or equal to 7.5 weight %, and less than or equal to 15 weight %, based on a total weight of the personal care composition or the emulsifying system thereof.

In at least one implementation, a weight ratio of one surfactant or emulsifier to another surfactant or another emulsifier in the emulsifying system may vary from about 0.5:1 to about 1.5:1. For example, the weight ratio of any one surfactant/emulsifier to another surfactant/emulsifier in the emulsifying system may be from about 0.5:1, about 0.6:1, about 0.7:1, about 0.8:1, or about 0.9:1 to about 1:1, about 1.1:1, about 1.2:1, about 1.3:1, about 1.4:1, or about 1.5:1.

In a preferred implementation, the personal care composition and the emulsifying system thereof may include a combination of at least two or more nonionic surfactants and/or emulsifiers. For example, the personal care composition may include one or more fatty or higher alcohols and one or more nonionic surfactants. In another example, the personal care composition may include one or more of glyceryl monostearate or glyceryl stearate, PEG-100 stearate, cetyl alcohol, stearyl alcohol, or combinations thereof. In a preferred implementation, the personal care composition and the emulsifying system thereof may include a combination of glyceryl monostearate, PEG-100 stearate, and cetyl alcohol. In the preferred implementation, including the combination of glyceryl monostearate, PEG-100 stearate, cetyl alcohol, and cetyl-stearyl alcohol 50/50, the weight ratio of glyceryl monostearate to PEG-100 stearate may be from about 0.5:1 to about 2:1, about 0.8:1 to about 1.8:1, about 1:1 to about 1.2:1, or about 1:1. In at least one example, the amount of glyceryl monostearate and the amount of PEG-100 stearate may be substantially equal to one another (e.g., +/−1%, 2%, 3%, 5%, 10%, or more). In a preferred implementation, including the combination of glyceryl monostearate, PEG-100 stearate, and cetyl alcohol, each of glyceryl monostearate and PEG-100 stearate may, separately and independently, be present in an amount of greater than or equal to about 1 weight %, greater than or equal to about 1.25 weight %, greater than or equal to about 1.5 weight %, greater than or equal to about 1.75 weight %, greater than or equal to about 2 weight %, or greater than or equal to about 2.25 weight %, and less than or equal to about 10 weight %, or less than or equal to about 6 weight %.

Skin Care Agents

In some implementation, the personal care composition may include one or more skin care agents. Any suitable skin care agents that do not adversely affect the stability and/or efficacy of the personal care composition may be used. In at least one implementation, the skin care agent may include one or more emollients configured to maintain a soft, smooth, and pliable appearance to the skin. As is known by those skilled in the art, the emollients may function by remaining on the surface of the skin or in the stratum corneum to act as a lubricant, to reduce flaking, and/or to improve the appearance of the skin.

The skin care agents may generally include one or more polymers (e.g., olyvinylpyrrolidone), starches (e.g., tapioca starches, hydrophobically modified corn starch, such as DRY-FLO TS® CAS Nos. 68989-12-8, 68554-70-1, 9005-25-8, etc.), protein derivatives (e.g., derivatized hydrolyzed wheat protein), ethoxylated fatty ethers, cellulosics (e.g., hydroxyethylcellulose), or the like, or combinations thereof. Illustrative skin care agents may include, but are not limited to, esters comprising an aliphatic alcohol having about 2 to about 18 carbon atoms condensed with an aliphatic or aromatic carboxylic acid including about 8 to about 20 carbon atoms (e.g., isopropyl myristate, decyl oleate, cetearyl isononanate, etc.). The esters may be straight chained or branched. In a preferred implementation, the ester has a molecular weight of less than about 500.

Other skin care agents may include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, palmitamidopropyltrimonium chloride, or the like, or combinations thereof. In a preferred implementation, the skin care agent is or includes a conditioner, such as a cationic cellulose polymer (e.g., polyquaternium-7).

Additional Optional Components/Ingredients

The personal care composition may include one or more additional optional ingredients. Illustrative optional ingredients may include, but are not limited to, one or more dyes, fragrances, buffers, and buffering agents (e.g., inorganic phosphates, sulfates, and carbonates), preservatives, thickeners, viscosity modifiers, antioxidants, chelating agents (e.g., EDTA, phosphates, etc.), opacifiers, hydric solvents, hydrotropes, antimicrobials, or the like, or combinations thereof. In at least one implementation, the personal care composition may be free or substantially free of parabens.

Methods

The present disclosure may provide methods for preparing stable personal care compositions. Particularly, the present disclosure may provide methods for preparing stable, emulsion-based personal care compositions that are free or substantially free of silicone and silicone compounds. The present disclosure may also provide methods for preventing the separation of hydrophobic and hydrophilic phases in personal care compositions that are free or substantially free of silicone and silicone compounds when exposed to aging conditions. It should be appreciated by one having ordinary skill in the art that aging conditions may be provided or defined by the ICH Guidelines. The method may include preparing a hydrophobic phase and a hydrophilic phase, and contacting the hydrophobic phase with the hydrophilic phase. For example, the method may include preparing the hydrophobic phase including one or more of the components disclosed herein, preparing the hydrophilic phase including one or more of the components disclosed herein, and mixing, combining, stirring, emulsifying, or otherwise contacting the hydrophobic phase and the hydrophilic phase with one another. The method may also include heating the hydrophilic phase and/or the hydrophobic phase while mixing, combining, stirring, emulsifying, or otherwise contacting the hydrophobic phase and the hydrophilic phase with one another. The hydrophobic phase and/or the hydrophilic phase may be heated at a temperature of from about 60° C. to about 90° C., about 65° C. to about 85° C., about 70° C. to about 80° C., or about 75° C. to about 80° C. The method may also include preparing an emulsifying system including one or more surfactants and/or emulsifiers to enhance the stability of the personal care composition. The method of preparing the emulsifying system may include mixing, combining, stirring, or otherwise contacting the one or more surfactants and/or emulsifiers with one another. For example, the method of preparing the emulsifying system may include mixing, combining, stirring, or otherwise contacting one or more amino acid surfactants, such as a glutamate surfactant (e.g., sodium stearoyl glutamate), glyceryl monostearate, PEG-100 stearate, and cetyl alcohol with one another.

The present disclosure may provide methods for predicting or preliminarily determining the stability of a personal care composition. The method may include exposing the personal care composition to one or more heating and cooling cycles. In at least one implementation, the method includes exposing the personal care composition to at least two heating and cooling cycles via a differential scanning calorimeter or differential scanning calorimetry (DSC). It should be appreciated that a DSC may determine the electrical energy input rate necessary to establish zero temperature differences between a substance and a reference material against either time or temperature as they are both subjected to a controlled temperature change. The method may include comparing the DSC curves of each of the heating and cooling cycles with one another. Comparing the DSC curves may include comparing trends or overlaps between the DSC curves of each of the heating and cooling cycles with one another, where similar or substantially similar trends or overlap or substantial overlap may indicate that the personal care composition is stable at when exposed to accelerated aging conditions. Comparing the DSC curves may include comparing peak intensities of the DSC curves of each of the heating and cooling cycles with one another, where substantial and/or significant changes in the peak intensities may indicate that the personal care composition is not stable after exposure to accelerated aging conditions. The method may also include outputting the stability of the personal care composition. Any one or more of the steps described above may be performed by an electronic processor.

All ingredients for use in the compositions described herein should be topically acceptable. As used herein, "topically acceptable" may refer any ingredient that is present in a composition as described in an amount and form which does not render the composition unsafe for use on surfaces of skin.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

A control personal care composition (C) and test personal care compositions (1)-(21), namely emulsion-based skin moisturizing compositions, were prepared by combining the ingredients/components according to Tables 1A, 1B, and 1C. Particularly, the amount of glyceryl monostearate, sodium stearoyl glutamate, PEG-100 stearate, and cetyl alcohol were combined as provided in Tables 1A, 1B, and 1C, and the remaining components were combined according to the ranges as provided in Table 1D. Generally, the ingredients/components of each of the control personal care composition (C) and test personal care compositions (1)-(21) were combined according to the ranges disclosed in Table 1E.

TABLE 1A

Personal Care Compositions (1)-(8) Weight (%)

| COMPONENT | 1 | 2 | 3 | 4 | 5 | 6 | 7 | 8 |
|---|---|---|---|---|---|---|---|---|
| Glyceryl Monostearate | 4 | 2 | 3.2 | 2 | 2 | 4 | 2.3 | 4 |
| Sodium Stearoyl Glutamate | 0.1 | 0.1 | 0.1 | 0.1 | 0.1 | 0.1 | 0.1 | 0.17 |
| PEG-100 Stearate | 4 | 2.6 | 3.0 | 4 | 2 | 2 | 2.4 | 2.1 |
| Cetyl Alcohol | 3.9 | 4 | 3.4 | 3.2 | 3 | 4 | 3 | 3 |

TABLE 1B

Personal Care Compositions (9)-(16) Weight (%)

| COMPONENT | 9 | 10 | 11 | 12 | 13 | 14 | 15 | 16 |
|---|---|---|---|---|---|---|---|---|
| Glyceryl Monostearate | 2.5 | 2.5 | 2.6 | 3.6 | 3.2 | 3.2 | 2 | 2 |
| Sodium Stearoyl Glutamate | 0.19 | 0.19 | 0.19 | 0.20 | 0.21 | 0.21 | 0.25 | 0.25 |
| PEG-100 Stearate | 2 | 2 | 2.7 | 4 | 3.1 | 3.1 | 3.0 | 3.0 |
| Cetyl Alcohol | 3.6 | 3.6 | 3.4 | 3 | 4 | 4 | 3.2 | 3.2 |

TABLE 1C

Personal Care Compositions (16)-(21) Weight (%)

| COMPONENT | 17 | 18 | 19 | 20 | 21 | C |
|---|---|---|---|---|---|---|
| Glyceryl Monostearate | 2.5 | 2 | 4 | 3.0 | 2.2 | 4 |
| Sodium Stearoyl Glutamate | 0.3 | 0.3 | 0.3 | 0.3 | 0.3 | 0 |
| PEG-100 Stearate | 4 | 2 | 3.1 | 2 | 3.2 | 4 |
| Cetyl Alcohol | 3.8 | 4 | 3.5 | 3 | 4 | 4 |

TABLE 1D

Remaining Components of Personal Care Compositions (1)-(21)

| COMPONENT | Range |
|---|---|
| Water | 72-80 |
| Propylene Glycol | 5.5-6.5 |
| Caprylyl Glycol | 0.2-0.4 |
| Sodium Benzoate | 0.4-0.6 |
| Lactic Acid | 0.2-0.4 |
| Glycerin | 0.05-0.2 |
| Petrolatum | 4.5-5.5 |
| Isopropyl Palmitate | 1-2 |
| Lexfeel D4(Neopentyl Glycol Diheptanoate (and) Isododecane)) | 0.5-1.5 |
| Dimethicone | 0-1.5 |

TABLE 1E

Amount of Components in Personal Care Compositions (1)-(21)

| COMPONENT | Range |
|---|---|
| Water | QS |
| Humectants | 5.95-7.5 |
| Preservatives | 0.4-0.6 |
| Anionic Surfactants | 0-0.3 |
| Non ionic surfactants | 3-9 |
| Fatty Alcohols | 2.5-4.5 |
| Emollient/Skin conditioning agent | 6-8 |

Example 2

The stability of each of the control personal care composition (C) and test personal care compositions (1)-(21) prepared in Example 1 was evaluated. Particularly, the stability of each of the control personal care composition (C) and test personal care compositions (1)-(21) of Example 1 was evaluated by measuring or observing the pH, the initial viscosity, stability under accelerated aging conditions, whiteness, absorbability, separation, spreadability, tackiness, greasiness, viscosity at about −30° C. for 5 days, and viscosity at −10° C. for 5 days.

To evaluate the viscosity under varying aging conditions, each of the control personal care composition (C) and test personal care compositions (1)-(21) was placed in a respective 4 oz. glass jar and exposed to an environment maintained at the particular conditions (e.g., time and temperature) indicated in Table 2. After the respective times of each of the studies elapsed, each of the samples was removed from the environment and allowed to cool in a monitored stability chamber maintained at about 25° C. After cooling to about 25° C., the viscosity and pH were measured, and the samples were observed/evaluated visually. Viscosity was measured using a Brookfield rheometer with spindle T-E at 5 RPM for about 1 minute.

To evaluate whiteness, absorbability, tackiness, spreadability, and greasiness, a Small Sensory Panel of ten panelists for sensory properties was utilized. Each of the ten panelists assessed each of the control personal care composition (C) and test personal care compositions (1)-(21) by using a standardized methodology and a 0 to 5 point assessment scale, where '0' represented the lowest level (i.e., none or low) and '5' represented the highest value. A controlled amount of each of the control personal care composition (C) and test personal care compositions (1)-(21) was applied for the analysis.

The results of the stability analysis of the control personal care composition (C) and test personal care compositions (1)-(21) are summarized in Table 2.

TABLE 2

Stability of Control and Test Personal Care Compositions (C) and (1)-(21)

| # | Initial$^A$ Viscosity (cP) | Viscosity$^A$ 5 days @ 30° C. | Viscosity$^A$ 5 days @ 10° C. | Separation$^B$ Under Accelerated Aging Conditions | pH | W$^C$ | S$^C$ | T$^C$ | G$^C$ |
|---|---|---|---|---|---|---|---|---|---|
| 1 | Pass | Pass | Pass | Fail | Pass | 3.7 | 2.9 | 2.1 | 3 |
| 2 | Fail | Pass | Pass | Fail | Pass | 1.9 | 3.2 | 1.5 | 1.8 |
| 3 | Pass | Pass | Pass | Fail | Pass | 3.2 | 3 | 2.2 | 2.1 |
| 4 | Fail | Pass | Pass | Fail | Pass | 2.6 | 4 | 2.1 | 2.2 |
| 5 | Fail | Fail | Fail | Fail | Pass | 2.1 | 3.5 | 2.6 | 2.5 |
| 6 | Pass | Pass | Pass | Pass | Pass | 2 | 3.2 | 2.2 | 1.7 |
| 7 | Fail | Pass | Pass | Fail | Pass | 2.3 | 3.8 | 2.2 | 2.1 |
| 8 | Pass | Pass | Pass | Fail | Pass | 2.7 | 3.3 | 2.2 | 1.9 |
| 9 | Fail | Pass | Pass | Fail | Pass | 1.9 | 3.6 | 1.6 | 2.2 |
| 10 | Pass | Fail | Pass | Fail | Pass | 2.7 | 3.8 | 2.3 | 2 |
| 11 | Fail | Pass | Pass | Fail | Pass | 2.3 | 3.7 | 2.4 | 2.2 |
| 12 | Fail | Pass | Pass | Pass | Pass | 3.8 | 2.8 | 2.2 | 2.3 |
| 13 | Pass | Pass | Pass | Pass | Pass | 3.4 | 3 | 2.4 | 2 |
| 14 | Pass | Pass | Pass | Pass | Pass | 2.7 | 3.4 | 2.5 | 2.3 |
| 15 | Fail | Pass | Pass | Fail | Pass | 3 | 3.6 | 2.6 | 2.4 |
| 16 | Fail | Pass | Pass | Fail | Pass | 3.1 | 3 | 2.2 | 2.3 |
| 17 | Fail | Fail | Pass | Fail | Pass | 4.1 | 2.8 | 2.5 | 2 |
| 18 | Pass | Pass | Pass | Fail | Pass | 2.5 | 3.5 | 1.9 | 2 |
| 19 | Pass | Pass | Fail | Pass | Pass | 3.1 | 3.1 | 2.5 | 2.2 |
| 20 | Pass | Pass | Pass | Pass | Pass | 2.9 | 3.4 | 1.9 | 1.9 |
| 21 | Pass | Fail | Pass | Fail | Pass | 3.3 | 3.2 | 2.5 | 1.8 |
| C | Pass | Pass | Pass | Pass | Pass | 2.5 | 3 | 1.8 | 2.4 |

$^A$ Fail = Not within acceptable range; Pass = Within acceptable range
$^B$ Fail = Phase Separation; Pass = No Separation
$^C$W = Whiteness; S = Spreadability; T = Tackiness; G = Greasiness As illustrated in Table 2, personal care compositions (6), (8), (13), (14), and (19), which did not include silicone (e.g., dimethicone), surprisingly and unexpectedly exhibited an initial viscosity of greater than 120,000 cP, a pH of from 4.2 to 4.6, no separation at accelerated aging conditions, spreadability of greater than 3.0, greasiness of less than 2.5, and no separation after aging for 5 days at about 30° C. As further illustrated in Table 2, personal care compositions (6), (8), and (14), exhibited absorbability of greater than 2.7, and a whiteness of less than 2.7. It was surprisingly and unexpectedly discovered that when glyceryl monostearate was added in an amount relatively greater than the amount of PEG 100 stearate, a suitable personal care composition was achieved. Reducing PEG 100 stearate also resulted in reduced whiteness. Without being bound by theory, it is believed that the high HLB value of sodium stearoyl glutamate facilitated balancing of the oil phase and surfactant values when reducing the amount of the other components in the personal care composition.

Example 3

Figure 1:
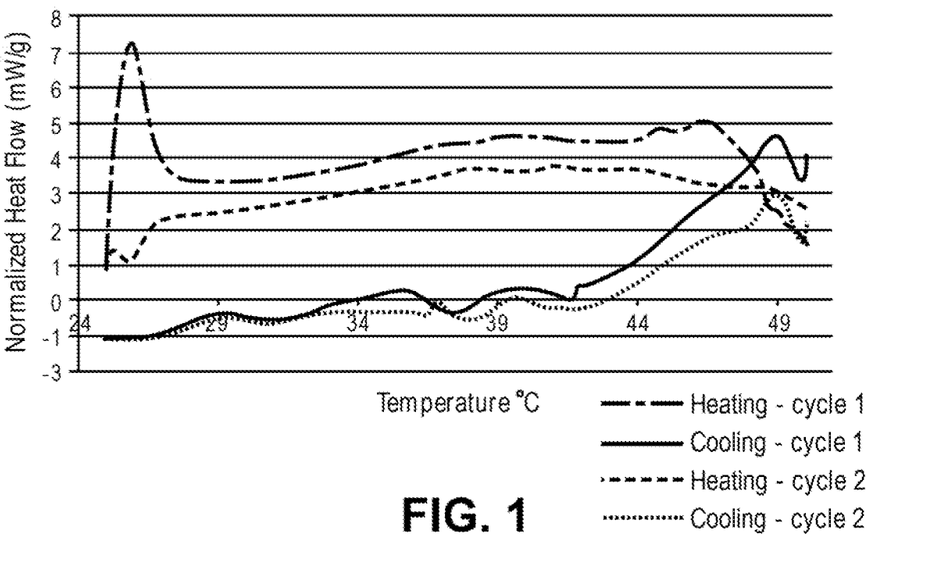
FIG. 1 illustrates a differential scanning calorimetry curve illustrating a first and second heating and cooling cycle of personal care composition (4).
Figure 2:
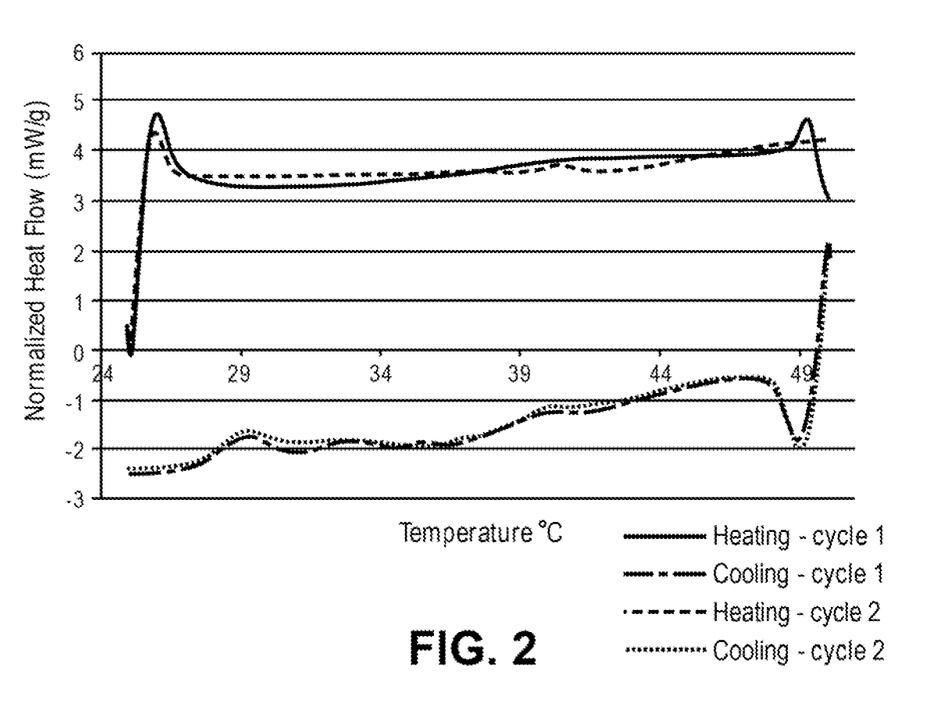
FIG. 2 illustrates a differential scanning calorimetry curve illustrating a first and second heating and cooling cycle of personal care composition (13).
Figure 3:
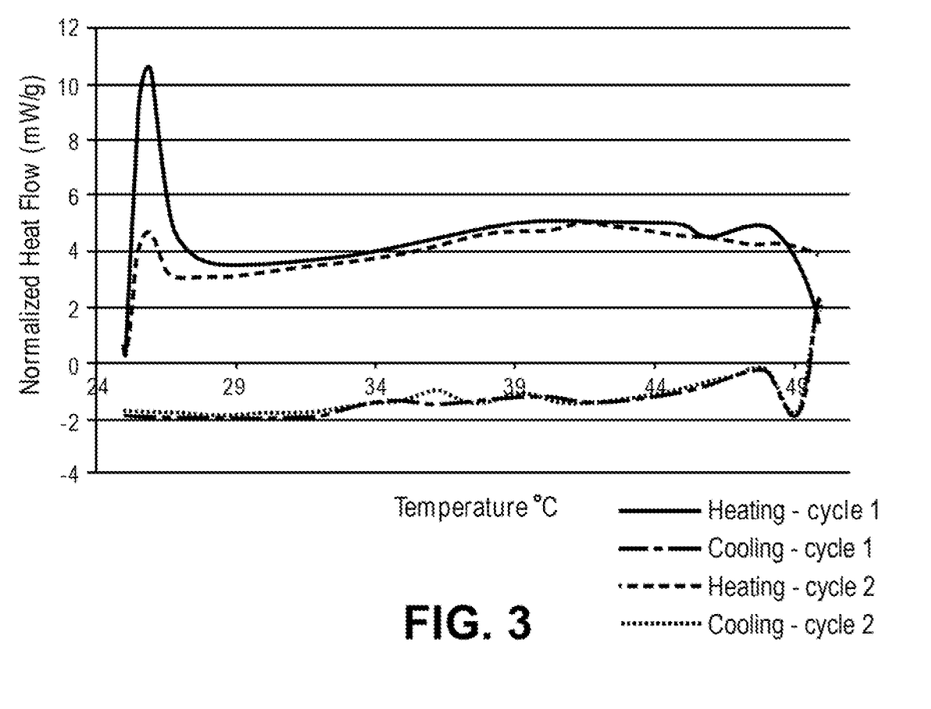
FIG. 3 illustrates a differential scanning calorimetry curve illustrating a first and second heating and cooling cycle of personal care composition (17).

Each of the control personal care composition (C) and test personal care compositions (1)-(21) prepared in Example 1 were evaluated by differential scanning calorimetry (DSC) via a differential scanning calorimeter to provide a predictive method for at least partially determining stability of the personal care compositions after exposure to accelerated aging conditions. To evaluate the personal care compositions (C) and (1)-(21), each of the samples was loaded into the differential scanning calorimeter and exposed to two heating and cooling cycle. The reference sample utilized was the control personal care composition (C). Representative DSC curves for each of the test personal care compositions (1)-(21) and the control personal care composition (C) are illustrated in FIGS. 1-3. Particularly, DSC curves for test personal care composition (4), (13), and (17) are illustrated in FIGS. 1-3, respectively.

As illustrated in FIG. 2, test personal care composition (13) exhibited substantially similar trends in the DSC curve. The DSC curves also exhibited substantial overlapping throughout each of the heating and cooling cycles. As determined in Example 2, the test personal care composition (2) was a stable composition that did not exhibit separation after exposure to accelerated aging conditions.

FIG. 1 which represents the DSC curves for test personal care composition (4) exhibited different trends in the curves of each of the heating and cooling cycles. Without being bound by theory, it is believed that the different trend in the curves of each of the heating and cooling cycles indicates a change in the structure; and thus, resulted in a lack of stability and/or phase separation.

FIG. 3, which represents the DSC curves for test personal care composition (17) exhibited changes in peak intensity in each of the heating and cooling cycles. Without being bound by theory, it is believed that the change in the peak intensities indicates a change in the structure; and thus, resulted in a lack of stability and/or phase separation.

The DSC curves illustrated in FIGS. 1-3 demonstrated a correlation between the DSC curves and the stability of personal care compositions after exposure to accelerated aging conditions, and thus, surprisingly and unexpectedly provides a method for predicting the stability of the personal care compositions that is reliable and relatively faster (i.e., about 4 hours) than testing under accelerated aging conditions.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A personal care composition, comprising an emulsion of a hydrophobic phase and a hydrophilic phase, wherein the hydrophobic phase comprises an emulsifying system comprising one or more amino acid surfactants;
   wherein the emulsifying system comprises glyceryl monostearate and PEG-100 stearate; and
   wherein the amount of glyceryl monostearate in the composition is relatively greater than the amount of PEG-100 stearate.

2. The personal care composition of claim 1, wherein the one or more amino acid surfactants comprise a glutamate surfactant.

3. The personal care composition of claim 2, wherein the glutamate surfactant is represented by formula (1):

wherein $R_1$ is a saturated or unsaturated, straight, or branched alkyl chain comprising 7 to 17 carbon atoms, and
wherein $M^+$ is each, independently, hydrogen, sodium, or potassium.

4. The personal care composition of claim 1, wherein glyceryl monostearate and PEG-100 stearate each, independently and separately, are present in an amount of at least 1.5 weight %, based on a total weight of the personal care composition.

5. The personal care composition of claim 1, wherein the emulsifying system further comprises one or more fatty alcohols, optionally, the fatty alcohols comprise cetyl alcohol, further optionally, the cetyl alcohol is present in an amount of from about 3 weight % to about 4 weight %, based on a total weight of the personal care composition.

6. The personal care composition of claim 1, wherein the hydrophobic phase further comprises a hydrophobic carrier, optionally, the hydrophobic carrier comprises petrolatum.

7. The personal care composition of claim 1, wherein the personal care composition is substantially free of dimethicone, optionally, wherein the personal care composition is substantially free of silicone and silicone compounds.

8. The personal care composition of claim 1, wherein the hydrophilic phase comprises water.

9. The personal care composition of claim 1, wherein the hydrophilic phase comprises one or more acids, optionally, the acids comprise lactic acid.

10. The personal care composition of claim 1, wherein the personal care composition has an acidic pH, optionally, the pH is from about 4 to about 6, further optionally, the pH is from about 4 to about 5.

11. The personal care composition of claim 1, wherein the personal care composition has a viscosity of greater than or equal to 50,000 centipoise (cP) at 25° C.

12. The personal care composition of claim 1, wherein the personal care composition does not exhibit phase separation after exposure to accelerated aging conditions.

13. The personal care composition of claim 1, wherein the personal care composition has any one or more of the following properties, as determined by an Small Sensory Panel using a standardized methodology and on a 0 to 5 point assessment scale:
   a whiteness of less than or equal to 2.7;
   an absorbability of greater than or equal to 2.7;
   a spreadability of greater than or equal to 3.0;
   a tackiness of less than or equal to 2.0;
   a greasiness of less than or equal to 2.5; or
   combinations thereof.

14. A method for preparing the personal care composition of claim 1, the method comprising: emulsifying the hydrophobic phase and the hydrophilic phase with one another, optionally, heating the hydrophobic phase and the hydrophilic with one another at a temperature of from about 60° C. to about 90° C., about 65° C. to about 85° C., about 70° C. to about 80° C., or about 75° C. to about 80° C.

* * * * *